United States Patent
Stigsson et al.

(10) Patent No.: US 9,499,767 B2
(45) Date of Patent: Nov. 22, 2016

(54) BIOREFINING OF CRUDE TALL OIL

(71) Applicant: SunPine AB, Pitea (SE)

(72) Inventors: Lars Stigsson, Bjarred (SE); Valeri Naydenov, Lulea (SE); Johan Lundback, Pitea (SE)

(73) Assignee: Sunpine AB, Pitea (SE)

( * ) Notice: Subject to any disclaimer, the term of this patent is extended or adjusted under 35 U.S.C. 154(b) by 0 days.

(21) Appl. No.: 14/653,470

(22) PCT Filed: Dec. 21, 2012

(86) PCT No.: PCT/SE2012/051490
§ 371 (c)(1),
(2) Date: Jun. 18, 2015

(87) PCT Pub. No.: WO2014/098692
PCT Pub. Date: Jun. 26, 2014

(65) Prior Publication Data
US 2015/0307810 A1    Oct. 29, 2015

(51) Int. Cl.
*C11B 3/00* (2006.01)
*C10G 3/00* (2006.01)
(Continued)

(52) U.S. Cl.
CPC ............. *C11B 3/006* (2013.01); *B01D 3/10* (2013.01); *B01D 3/143* (2013.01); *B01D 3/28* (2013.01); *C07C 4/04* (2013.01); *C07C 51/44* (2013.01); *C09F 1/02* (2013.01); *C10G 3/00* (2013.01); *C10G 3/50* (2013.01); *C10L 1/026* (2013.01); *C10L 1/08* (2013.01); *C10L 1/1888* (2013.01); *C10L 10/12* (2013.01); *C11B 3/008* (2013.01); *C11B 3/12* (2013.01); *C11B 11/00* (2013.01); *C11B 13/005* (2013.01); *C07C 2103/26* (2013.01); *C10G 2300/1014* (2013.01);

(Continued)

(58) Field of Classification Search
None
See application file for complete search history.

(56) References Cited

U.S. PATENT DOCUMENTS 3,644,179 A * 2/1972 Knoer ................ C11B 3/12
159/6.2
4,001,114 A   1/1977 Joseph et al.
(Continued)

FOREIGN PATENT DOCUMENTS

WO   WO 2009/131510 A1 * 10/2009
WO   WO 2012/069704       5/2012

OTHER PUBLICATIONS

Supplementary Partial European Search Report, Application No. EP 13 86 6067, Dated Jul. 18, 2016.

*Primary Examiner* — Yate K Cutliff
(74) *Attorney, Agent, or Firm* — Baker & Hostetler LLP

(57) ABSTRACT

A process for pre-treatment of a crude tall oil (CTO) for removal of impurities is disclosed. The process comprises a first pre-treatment step involving a CTO wash and a separation of a first oil phase comprising refined CTO and an aqueous phase holding impurities, and a second step involving a separation of a second oil phase from the aqueous phase. A process for refining of crude tall oil (CTO) is also disclosed. The process comprises fractionation under vacuum of a refined CTO into at least one stream of refined tall diesel (RTD) or tall oil fatty acids (TOFA) and at least one stream of resin acid(s) (RA). The stream of RTD or TOFA is deoxygenated forming hydrocarbon compounds in a subsequent step. This invention also relates to a refined tall diesel. Furthermore, a process for the production of a refined tall diesel (RTD) composition, wherein crude sulphate turpentine(s) (CST) is added to the refined tall diesel (RTD) composition, is described.

26 Claims, 2 Drawing Sheets

Figure 1:
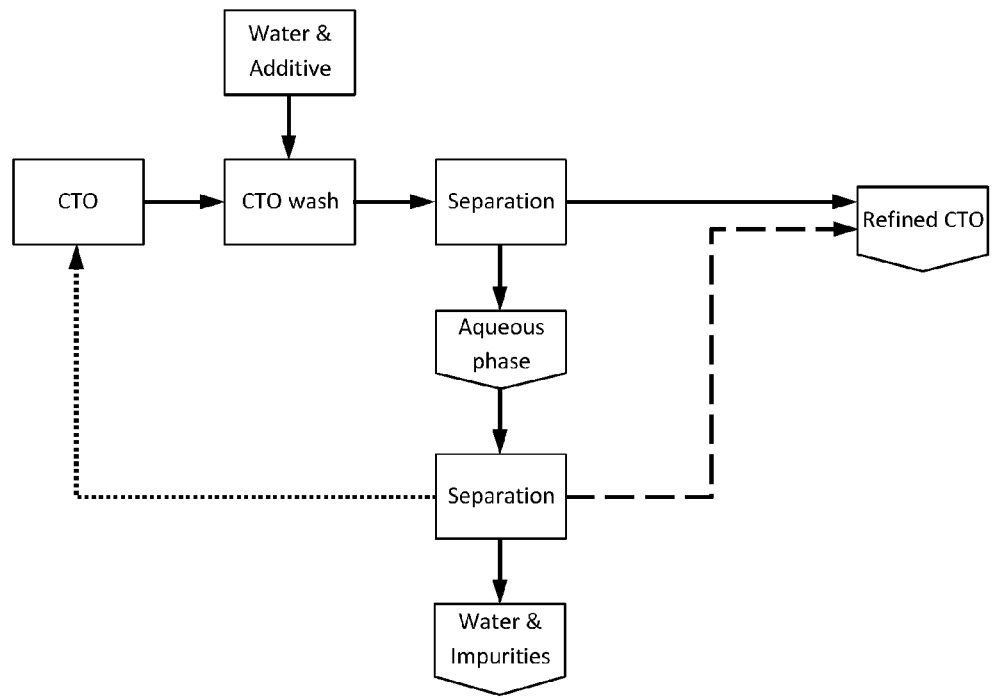

(51) Int. Cl.
| | |
|---|---|
| *C07C 4/04* | (2006.01) |
| *C10L 10/12* | (2006.01) |
| *C07C 51/44* | (2006.01) |
| *B01D 3/10* | (2006.01) |
| *B01D 3/14* | (2006.01) |
| *B01D 3/28* | (2006.01) |
| *C09F 1/02* | (2006.01) |
| *C11B 3/12* | (2006.01) |
| *C11B 11/00* | (2006.01) |
| *C11B 13/00* | (2006.01) |
| *C10L 1/02* | (2006.01) |
| *C10L 1/188* | (2006.01) |
| *C10L 1/08* | (2006.01) |
| *C10L 1/16* | (2006.01) |

(52) U.S. Cl.
CPC ...... *C10L1/1616* (2013.01); *C10L 2200/0469* (2013.01); *C10L 2200/0484* (2013.01); *C10L 2270/026* (2013.01); *C10L 2290/543* (2013.01); *C10L 2290/544* (2013.01); *C10L 2290/545* (2013.01); *Y02E 50/13* (2013.01); *Y02P 30/20* (2015.11); *Y02W 30/74* (2015.05)

(56) References Cited

U.S. PATENT DOCUMENTS

| | | |
|---|---|---|
| 2010/0317903 A1 | 12/2010 | Knuuttila |
| 2011/0092724 A1 | 4/2011 | Mokkila |
| 2012/0088943 A1* | 4/2012 | Knuuttila ............... C10G 45/58 585/310 |
| 2012/0123087 A1* | 5/2012 | Bowles ................ C11B 13/005 530/208 |

\* cited by examiner

BIOREFINING OF CRUDE TALL OIL

CROSS-REFERENCE TO RELATED APPLICATIONS

This application is the National Stage of International Application No. PCT/SE2012/051490, filed Dec. 21, 2012, the disclosure of which is incorporated herein by reference in its entirety.

FIELD OF THE INVENTION

The present invention relates to the biorefining of crude tall oil (CTO).

TECHNICAL BACKGROUND

The term Crude Tall Oil, in the following CTO, refers to a by-product stream obtained during pulping of wood in the Kraft pulping process. The name tall oil (TO) originated as anglicisation of Swedish "tallolja" ("pine oil"). The TO comprises of fraction having acidic properties (—COOH functional group) typically about 75-80 wt. % and neutral fraction up to 25 wt. %. The latter fraction is often referred to as unsaponifiable fraction. The unsaponifiable fraction comprises of wide spectrum of components such as hydrocarbons, fatty alcohols, phytosterol-type alcohols, aldehydes, etc. as well as high molecular weight components originating from internal reactions between constituents of acidic and neutral fractions. The fraction comprised of components with acidic functionality on the other hand, can be further subdivided into two large fractions namely, (i) fatty acids fraction and (ii) resin acids fraction each containing a number of individual components. From this description of the tall oil composition it is obvious that the CTO represents an attractive pool of renewable fine chemicals, which are nowadays gaining much attention in view of stringent environmental regulations and rising prices of fossil oils.

At present, CTO fractionation is done typically by vacuum distillation. The objectives are rather straight forward, to split the CTO into two fractions (i) acidic fraction up to 75 wt. % and fraction of less importance called (ii) tall oil pitch (TOP). The acidic fraction is further processed in a sequence of fractionation towers operating at high temperatures and relatively high vacuum to obtain streams enriched in fatty acids and resin acids. TOP is typically returned to the pulp mills as internal fuel or used as biofuel in heat and power plants. It is important to minimize the fraction of TOP produced in CTO refining processes and the present invention is directed to a CTO refining process with high yield of valuable chemicals and biofuels for automotive use.

A process for refining CTO into valuable biofuels is disclosed in WO 2009/131510. In WO 2009/131510 there is disclosed a method for conversion of crude tall oil into high-quality diesel fuels comprising the steps of (a) removal of non-oil contaminants present in the crude tall oil and recovering valuable organic compounds present in the crude tall oil, thereby forming a refined tall oil stream; (b) removal of the volatile fraction of the refined tall oil stream from step a), thereby forming a volatiles free oil stream comprising organic components with boiling points, at atmospheric pressure, of 170° C. or higher; (c) separation in a vacuum fractionation tower of the volatiles free oil stream of step b) into two process streams or phases wherein a first process stream or phase is substantially comprising components with boiling points, at atmospheric pressure, in the range of 170-400° C. and a second process stream or phase is substantially comprising components with boiling points, at atmospheric pressure, over 400° C.; and (d) lowering the oxygen content in the stream comprised of components with boiling points in the range 170-400° C. from step c) by decarboxylation and/or decarbonylation.

One aim of the present invention is to provide an improved way of refining CTO. Another specific goal according to the present invention is to provide an improved pre-treatment process of CTO. Yet another specific target of the present invention is to provide an improved process for the production of resin acids and refined tall diesel (RTD in the following) from CTO. There are also other aims of the present invention which are presented below.

Background to a First Aspect of the Invention

Tall oil rosin (or resin acids) produced via vacuum distillation of CTO finds use as an essential component of adhesives, rubbers, inks, and emulsifiers, whereas tall oil fatty acids (TOFA) find use in the production of soaps and lubricants.

Crude tall oil, however, being a residue stream from Kraft pulping operations contains a long list of impurities. Typical CTO contaminants include residual mineral acid, alkali salts and/or soaps, alkaline earth metal salts and/or soaps, transition metals, cellulosic fibers and large organic lignin compounds with molecular weights well over 1000 units. The presence of impurities is usually caused by ineffective tall oil separation from salty brine during the CTO production at the Kraft pulp mill. The small amount of brine which follows the CTO contains most of the above impurities.

The impurities cause problems during the CTO processing and have detrimental effect on the yield of desired fractions, namely RTD, TOFA and tall oil resin acids (RA). Thus, different types of salts and/or soaps, cellulosic fibers and lignin deposit on various heating surfaces causing flow problems and/or limit the heat transfer. Further, the salts cause splashing within thin-film evaporator units (TFE) offering a chance for non-volatile components to be entrained in the gas phase. The residual mineral acid (typically sulphuric acid), various salts and transition metals act as catalysts during CTO storage and processing. The $H_2SO_4$ is a highly effective catalyst in esterification reactions between free fatty acids (FFA) and various components from the neutral fraction possessing a (—OH) functional group. The obtained esters are typically characterized by high molecular weight thus ending up in the less desirable TOP fraction. These high molecular weight esters are typically formed during CTO storage. During CTO processing, the sulphuric acid attacks double bonds within FFA which leads to polymerization products of high molecular weight also ending up in the TOP. Sulphuric acid is also an active catalyst for resin acid decarboxylation producing the corresponding hydrocarbon and hence substantially decreasing the yield of tall oil resin acids. Depending on the process layout/equipment, the obtained hydrocarbons end up either in the RTD/TOFA or in the resin acid fraction in both cases decreasing the quality of the respective fraction. Various types of salts and especially the transition metals are also very active catalysts for activation of double bond functionality and resin acid decarboxylation.

During the years efforts have been made to remove impurities in the CTO prior to fractionation. The most successful approach up to now seems to be the so called CTO depitching, where the incoming oil stream is passed through a TFE unit where it is subjected to fast heating and most of the FFA and resin acids are volatilized and processed further to obtain the individual TOFA and tall oil resin acid fractions. Within this approach most of the impurities follow the TOP stream collected at the TFE bottom. Despite the short thermal treatment a substantial part of the CTO components undergo undesirable reactions promoted by the impurities as described earlier. In addition, some of the impurities are entrained in the produced vapours.

CTO pre-treatment described in the first embodiment of the present invention contributes to the removal of typical CTO impurities. The absence of CTO impurities during refining steps of the present invention leads to preservation of the desirable CTO components and hence higher yields for RTD/TOFA and RA products and even TOP of better quality. Furthermore, the RA fraction will be of higher grade in terms of colour and/or isomer distribution since colour bodies are related to detrimental effects caused by the impurities, whereas RA isomerisation is promoted by the CTO impurities in combination with the elevated temperatures needed for the fractionation.

Technical solutions described within the second aspect of the present invention contribute to beneficial synergy for the production of RTD fraction and RA fraction of superior quality. The solutions allow an energy efficient process compared to prior art. The large energy consumption used for the refining of TOFA is omitted when producing RTD in accordance with the present invention. Moreover, the innovative fractionation sequence allows for the efficient separation of biofuels (RTD) and fine chemicals (RA) compared to the exhausting and energy intensive distillation steps commonly used in CTO fractionation processes.

The third aspect of the present application relates to the use of crude sulphate turpentine (CST) which seeks to maximise further the RTD yield and improves the RTD composition by (i) decreasing the density of the resulting composition and (ii) improving the balance of the boiling point (BP) distribution. Thus RTD without CST has rather narrow BP distribution 340-400° C. (about 90 wt. % of the RTD has boiling points in this range), whereas RTD composition with CST has a more even BP distribution 140-400° C. (CST itself comprises of range of components which combined with TO heads (sesqui- and di-terpenes along with the light FA C12-C16) is filling-in the whole BP range for the final RTD product)).

In the following we describe a process for improved tall oil refining and fractionation into high-value fractions obtained in higher yields and better quality compared to previous art.

Summary of a First Aspect of the Invention

As mentioned above, according to a first objective of the present invention there is presented an improved process for the removal of impurities from a CTO.

This aim is obtained by a process for the pre-treatment of a crude tall oil (CTO), said process comprising a first pre-treatment step involving a CTO wash and a separation of a first oil phase comprising refined CTO and an aqueous phase holding impurities, and a second step involving a separation of a second oil phase from the aqueous phase. As understood from above, this aspect of the present invention relates to the efficient removal of typical crude tall oil impurities such as residual mineral acid, alkali, alkali earth metal salts/soaps, transition metals, fibers/foreign matter and lignin compounds to produce refined tall oil. Therefore, according to one embodiment of the process for the pre-treatment of a CTO according to the present invention, the fibers, salts, residual inorganic acid and/or lignin constitute the impurities. The residual inorganic acid is the acid utilised at pulp mills to convert tall oil soap into tall oil, often being sulphuric acid.

It should further be said that other important aspects of the present invention are e.g. separation of a volatile fraction from the refined tall oil and the fractionation of volatiles free tall oil to streams comprised of a) components boiling in the diesel range (RTD); b) high quality resin acids (RA) and c) heavy molecular weight fraction (tall oil pitch, TOP) of superior quality particularly suitable as energy source within a broad range of industrial applications.

Specific Embodiments of a First Aspect of the Invention

According to a first aspect of the present invention the CTO stream is pre-treated for removal of contaminants prior to fractionation. In one embodiment of the CTO pre-treatment process, the CTO is contacted with water in a CTO wash step wherein the amount of water used is less than about 5 wt. % (on incoming CTO). The wash water may contain additives. According to the present invention, the contact between CTO and washing liquid may be performed by a dynamic mixer. It should however be said that any piece of equipment which is able to provide an intimate contact between CTO and the aqueous phase is suitable according to the present invention. The means for providing effective mixing is essential due to the low amount of wash water. The wash water targets the removal of some of CTO impurities (inorganic salts and residual acid ($H_2SO_4$)), whereas water additive targets the removal of other impurities such as transition metals and various soaps. Further, the additive is modifying metal ions in order to enhance their preference towards the aqueous phase. As such, moderate mixing, for example a static mixer, does not provide the necessary contact according to the present pre-treatment process. Therefore, according to one specific embodiment, the CTO wash is performed by a mixing procedure giving intimate contact between CTO and the aqueous phase.

A parameter which facilitates the intimate contact between washing liquid and CTO is temperature. Thus according to one specific embodiment of the present invention the contact is affected at temperatures higher than 90° C. and preferably at about 95° C.

According to the invention, various additives may be added within the washing step thus assisting the removal of CTO impurities. One function of such additives may be to bind all metal ions within CTO. The binding is typically done through a complex formation between the targeted metal ion and the additive (within complex formation terminology often referred to as ligand(s)). The ligand(s) may range from ionic type to molecule type and hence variable pathways for the complex formation. According to the invention thus formed complex is water soluble. There are several ligand(s) which might be utilised as additive according to the invention. According to one specific embodiment, at least one chelating agent is added in the first pre-treatment step. The term "chelating agent" here specifies the way a complex is formed. Citric and ethylene-di-amine tetra-acetic (EDTA) acids are preferred chelating agents as these are commonly used also in other applications, and as they also cover a wide range of metal ions, i.e. not being specific for a certain ion.

As understood from above, the oil phase obtained according to the pre-treatment process is intended to be further processed. According to one specific embodiment of the present invention, the recovered second oil phase is fed into the first oil phase comprising refined CTO. As such the total yield for further processing is increased. Another option is to recycle the second oil phase back into the (unrefined) CTO storage. The objective of the recovery and/or recycle of the second oil phase into the first refined oil phase is to achieve a high CTO yield over the pre-treatment step. The CTO yield of this pre-treatment step (measured as in/refined CTO out) is higher than 96%, preferably higher than 98% by weight.

The separation of phases in the first and second pre-treatment steps can be performed by different process machinery according to the present invention. According to one specific embodiment, the separation of phases in the first pre-treatment step is performed in a separator unit where the separation is driven by centrifugal force. Other types of separation equipment alone or in combination can also be used, such as e.g. a combination of filtration and decantation. In this latter case, the filtration advantageously precedes decantation since lignin, fibres and other non-oil impurities may hinder the water phase separation. A process unit where separation is driven by centrifugal force on the other hand is the preferred process machinery as it efficiently separates aqueous phase and solid impurities from tall oil (TO) in very short time in compact single equipment. According to yet another specific embodiment of the present invention, the separation of phases in the second step is performed by decantation. For the stream intended in this step, the oil-water proportions are more even and the flow rate of this stream is much lower which open up the possibility to use decantation efficiently. It is advantageous to preserve the high temperature utilised during the first washing step since the temperature assists the separation in the second separation step Following removal of contaminants according to the principles described herein above, the refined CTO is further treated by removal of volatiles from the refined CTO stream. According to one specific embodiment of the present invention, the refined CTO obtained from the pre-treatment is fed into a process system providing separation of volatile components having boiling points below 170° C. in order to provide a "volatiles depleted tall oil stream". The process system used for removal of volatiles from the refined CTO stream may comprise unit combinations such a flash vessel-TFE (thin film evaporator) or a stripper type tower (packed column equipped with high surface area packing). A TFE is the most preferred process system for removal of volatiles from a refined CTO stream in accordance with the invention.

It is noted that there is a range of different volatile compounds that are removed in this step. Volatile compounds include water, various gases dissolved in water (if water is present), terpenes and various sulphurous compounds such as methylsulphide and methylmercaptan.

After removal of volatiles from the refined CTO stream, refined CTO substantially free from volatiles is fractionated into RTD/TOFA and RA by a vacuum distillation process system comprising one or more vacuum fractionation devices. This further processing of refined CTO into individual high-value fractions is further detailed below.

Background to a Second Aspect of the Invention

Crude tall oil contains a wide range of organic compounds including turpentine, resin acids, sterols (5-10%), fatty acids (mainly palmitic acid, oleic acid and linoleic acid), fatty alcohols, and other alkyl hydrocarbon derivates. By fractional distillation of CTO tall oil resin acids (RA) and tall oil fatty acids (TOFA) can be obtained. The RA finds use as a component of adhesives, rubbers, and inks, and as an emulsifier. The TOFA can be used as a feedstock for production of renewable diesel fuels for example RTD (crude tall diesel), fuel additives (cetane number enhancers) or be used as base material in production of fine chemicals (detergents, paints etc.).

The CTO contains more or less sulphur compounds in ranges from about 500 ppm up to several thousand ppm. The sulphur compounds, often highly odorous, include a wide range of organic and inorganic sulphur compounds including sulphate, sulphite, polysulfide, elemental sulphur, mercaptans, organic sulphides and organic sulfones and sulfonates. The sulphur compounds are primarily connected to low molecular weight components present in the crude tall oil (turpentine) but may be present in both the fatty and the diterpenic moieties of crude tall oil.

Pulp mills often utilize specialty chemicals to additionally enhance their pulp yield. A typical chemical utilized in Kraft type process is anthraquinone (AQ). Thus CTO imported from pulp mills utilising AQ contain certain portion of AQ up to 2000 ppm.

The CTO contains a significant portion of fatty acids herein also abbreviated FA. The FA comprise of components ranging from C12 up C26, where the C18 fatty acid isomers are principal components. The FA's have two functional group types carboxyl group and double bonds. The FA components range from saturated to components with varying degree of unsaturation up to three double bonds (isolated or conjugated).

The crude tall oil also contains a significant portion of valuable C20 diterpenic acids (herein also abbreviated RA) including abietic acid, the aromatic dehydroabietic acid and sulphonic acid derivatives of the diterpenic acids formed by arene substitution. Diterpenic acids have two functional group types, carboxyl group and double bonds. Nearly all diterpenic acids have the same basic skeleton: a 3-ring fused system with the empirical formula $C_{19}H_{29}COOH$.

Diterpenic acids occur in pines in a number of isomeric forms having the molecular formula $C_{19}H_{29}COOH$ and in some related structures. The most prevalent diterpenic acids are:

Abietic-Type Acids
   abietic acid
   abieta-7,13-dien-18-oic acid
   13-isopropylpodocarpa-7,13-dien-15-oic acid
   neoabietic acid
   dehydroabietic acid
   palustric acid
   simplified formula $C_{20}H_{30}O_2$, or $C_{19}H_{29}COOH$
   represents the majority 85-90% of typical tall oil.
   structurally shown as $(CH_3)_4C_{15}H_{17}COOH$
   molecular weight 302
Pimaric-type Acids
   pimaric acid
   pimara-8(14),15-dien-18-oic acid
   levopimaric acid
   isopimaric acids
   simplified formula $C_{20}H_{35}O_2$ or $C_{19}H_{34}COOH$
   structurally represented as $(CH_3)_3(CH_2)C_{15}H_{23}COOH$
   molecular weight 307

The manufacture of wood pulp grade chemical cellulose using the Kraft chemical pulping processes releases these diterpenic acids into the spent cooking liquor.

Crude Kraft Turpentine (often CST, i.e. crude sulphate turpentine) is an organic liquid obtained as a residual product during Kraft pulping. The highly odorous crude Kraft turpentine is often handled in closed systems and collected at the pulp mill site and burnt as fuel or exported for upgrade. Turpentine may also be obtained by the fractionation of crude tall oil or by the distillation of resin obtained from trees, mainly pine trees. Turpentine fractions comprise of a wide range of organic compounds often called terpenes. The terpenes are classified in terms of number of isoprene units C5H8 needed to build-up the respective component and hence hemi-(C5H8), mono-(C10H16), sesqui-(C15H24) diterpenes (C20H32) and so on. Turpentine fractions from CTO are typically boiling in the range of 120-180° C. at atmospheric pressure, where mono-terpenes such as alpha- and beta-pinene are principle components. Turpentine's have a density of 0.7-0.87 kg/l.

Summary of a Second Aspect of the Invention

The present invention is also directed to the conversion of CTO (crude tall oil) optionally comprising turpentine, fatty acid and resin acid (RA) fractions into a renewable diesel fuel (refined tall diesel (RTD)) or TOFA and purified resin acids (RA)). According to this aspect of the present invention there is provided a process for the combined production of RTD/TOFA and RA from crude tall oil (CTO), said process directed to the refining of CTO, wherein the process comprises fractionation under vacuum of a refined CTO into at least one stream of refined tall diesel (RTD) or TOFA, said RTD or TOFA comprising from 2-40% by volume of resin acids and from 20-90% by volume of fatty acids, and at least one stream of resin acid(s) (RA) comprising less than 5% by volume of fatty acids, wherein the stream of RTD or TOFA optionally in a subsequent step is deoxygenated forming hydrocarbon compounds.

The remaining TOP (after recovery of RTD/TOFA and RA) fraction constitutes less than 30% by weight of the CTO fed to the fractionation stages.

Prior to fractionation, the CTO is advantageously pre-treated and converted to refined CTO in accordance with the first aspect of the present invention discussed herein above. In a first pre-treatment step, the CTO is treated for removal of contaminants by centrifugation and/or filtering, followed by a step for removal of water and volatiles thereby forming a refined CTO stream. In a second step, high boiling point (heavy by molecular weight) components are separated as liquid stream (tall oil pitch, TOP) under vacuum from the gaseous stream mainly comprised of fatty and resin acids.

Gaseous fatty and resin acids are drawn into a fractionation tower operating under vacuum wherein a RTD/TOFA fraction rich in fatty acids is withdrawn from the upper part of the tower and a RA rich fraction is withdrawn from the bottom of the tower. The gaseous fatty acid rich RTD/TOFA stream is condensed into liquid refined tall diesel "RTD", which RTD may be exported for further upgrade to, for example, premium biofuel components. Alternatively the RTD/TOFA stream, with or without further refining for lowering the RA content, is exported for use in fine chemicals manufacturing (soaps, lubricants, adhesives and varnishes).

In another specific embodiment of the present invention, organic compounds originating from wood processing and boiling in the range of 120-180° C. (including for example turpentine), is imported and added to the RTD. Organic compounds (including turpentine) can also be recovered from the volatiles fraction removed in accordance with the description herein above and, advantageously, be added to RTD. Turpentine compounds (with principal components alpha- and beta-pinene) have a rather low density and such addition to the RTD decreases the overall density of RTD. This addition of turpentine and/or other organic chemicals originating in the processing of wood processing and boiling in the range of 120-170° C. is further described below and relates to a third aspect of the present invention.

In an optional fourth step RTD, with or without turpentine chemicals added, is treated under catalytic conditions in at least one reaction zone in a reactor operating at a temperature above 150° C. wherein fatty acids present in the RTD are decarboxylated and/or decarbonylated thereby forming renewable diesel range fuel components.

The use of strategically placed TFE's and CTO pre-treatment, where CTO impurities are removed, work together towards preservation of the desirable RTD/TOFA and RA components, which in turn increases RTD/TOFA and RA yields in comparison to prior art. Moreover, the use of fractionation towers operating at deep vacuum levels and characterized with minimal pressure drop profiles ensures low operating temperatures during fractionation thus providing an energy efficient process for CTO fractionation in comparison to prior art.

Specific Embodiments of a Second Aspect of the Invention

Below, specific embodiments are described relating to the process for the combined production of RTD/TOFA and RA from CTO according to the present invention.

The inventors have discovered that CTO can be transformed in a series of innovative steps into a stream of refined tall diesel (RTD) or TOFA and a stream of valuable Resin acids, (RA). RTD comprises mainly fatty acids, fatty alcohols and resin acids. The RTD is further characterized by the boiling points of the organic compounds in the RTD. RTD components boil in the range of 120-420° C., more preferred in the range of 160-400° C. at atmospheric pressure and the typical RTD mixture has a density of 0.88 to 0.95 kg/l. The fatty acid rich stream may alternatively be exported and used as TOFA in manufacturing of fine chemicals.

As disclosed above, there may be one or more CTO pre-treatment steps performed before the actual fractionation under vacuum of a refined CTO and subsequent recovery of RTD/TOFA and RA rich streams.

CTO is optionally pre-treated by the procedures described herein followed by at least one separation treatment which removes the tall oil fraction comprised of components with boiling points below about 200° C., more preferably below about 170° C. at atmospheric pressure (in the following referred to as tall oil volatiles).

The volatile fraction present within CTO is typically in the range from a few tenths of wt. % up to 2 wt. % in addition to the 0.5-3 wt. % water entrained within the CTO. The former fraction is comprised of number of components with varying molecular weight primarily C8 to C16 carbon compounds (turpentine, hydrocarbons, hydrocarbons with varying content of heterogeneous elements such as sulphur, oxygen, nitrogen, etc.) Volatile organic material boiling at atmospheric pressure below about 200° C., but over about 120° C. is removed from the stream of crude tall oil. The volatiles (including turpentine) can be removed in one or more thin-film evaporators or strippers and combinations thereof operating at a temperature in the range of 100-220° C. and a low pressure in the range of 30-60 kPa.

In a following process step, the high-boiling point CTO components or tall oil pitch, TOP (residual ash, organic fraction with average boiling points of individual components well over 440° C.) are separated from RTD/TOFA components and resin acids present in the CTO. Apart from ash, tall oil pitch typically consists of (i) components comprising the unsaponifiable fraction (>C28); (ii) high-molecular weight (500-600 g mol$^{-1}$) esters of steryl- and/or wax-type and (iii) products of Diels-Alder-type intermolecular dimerization reaction. Typical high-boiling point compounds within the CTO unsaponifiables are Campesterol (C28), Stigmasterol and Sitosterol (C29), Squalene, Betulinol, Lupeol (C30), Methyl-Betulinol (C31), etc.

In one embodiment of the present invention, the TOP is separated from fatty and resin acids using one or more thin film evaporators (TFE) operating in parallel or in series at 250-320° C. and a low pressure of 0.7-1.5 kPa. Heat is supplied to the TFE by steam or hot oil. The temperature of the devolatilized tall oil (fatty acids and resin acids) exiting the TFE shall be in the range of 200-330° C., preferably 200-250° C., prior to charge into a fractionation tower equipped with one or more structured packing(s).

The main fractionation tower used for separation of RTD/TOFA and RA is operating under vacuum conditions (1-25 mbar, preferably 1-10 mbar) and at a temperature in the range 150-280° C. The main fractionation tower and its feed section design is optimized according to the following objectives: (i) maximum yield of RTD/TOFA fraction with components boiling in the temperature range 170-420° C. (at atmospheric conditions); (ii) distinct fractionation cut at about 370-420° C. (at atmospheric conditions); (iii) minimum undesired reactions in order to recover resin acids in high quality and yield in the lower part of the tower and (iv) lowest pressure and temperature in the bottom section of the fractionation tower, which minimizes the degradation of desirable product components.

As may be understood from above, according to one specific embodiment, the fractionation under vacuum is performed in at least three steps (TFE for removal of TOP from refined CTO, a fractionation tower separating RTD/TOFA and RA and a fractionation tower for refining RA).

According to the specific embodiment disclosed above CTO (refined by procedures described herein) is charged to a first fractionation step for separation of tall oil pitch (TOP) from CTO followed by a second fractionation step (a vacuum fractionation tower) wherein a stream rich in RTD components having a boiling point at atmospheric pressure in a range of 170-420° C. is separated from a stream of RA components having a boiling point above about 420° C. at atmospheric pressure. In a third fractionation step RA is further refined into RA with a low fatty acid content.

By the utilization of TFE units for the removal of tall pitch from CTO levels of less than 5% resin acids remaining in tall oil pitch can be achieved. The gaseous fatty acid and resin acid rich stream exiting the TFEs is discharged into the main fractionator designed for separation of RTD components and resin acids. In an alternative and preferred configuration, refined CTO is charged to a first TFE discharging volatilised TOFA and RA into the main fractionator and discharging RA rich and TOFA arm CTO into a second TFE discharging FA and RA into the main fractionator and a RA stream still rich in RA which stream is charged to a third TFE discharging RA into a RA purification step (RA polishing tower) and discharging TOP for export from the plant.

According to one specific embodiment, the RA rich stream recovered from the lower section of the fractionation tower is discharged into the RA purification step (polishing tower) or further processed in a thin-film evaporator for separation of entrained TOP components from RA(s), said RA(s) being further refined by processing under vacuum in the RA purification step (RA polishing tower) in order to produce high quality RA(s) comprising less than about 4 wt. % fatty acids.

A packed fractionation tower is typically comprised of one or more beds of structured packing, a reboiler arrangement in the bottom part of the column and preferably a reflux arrangement at the top part of the column.

Modern structured packing typically consists of thin corrugated metal plates or gauzes arranged in appropriate fashion, where the general purpose of each particular design is to force the fluids pumped into the column to follow these long pre-designed paths thereby providing a large surface area which in turn ensures maximum contact between the fluids and the vapours. Although superior relative to tray-type distillation columns, the packed bed columns also show certain pressure drop. Utilization of specially designed structured packing ensures that the achieved pressure drop within the column top and bottom is below 15 mbar, preferably 10 mbar and most preferred 5 mbar.

According to preferred embodiments of the present invention, structured packing(s) characterized with minimal pressure drop are utilized.

The height of the structured bed is closely related to the desired fractionation degree i.e. the number of theoretical stages needed in order to achieve certain level of fractionation. As may be understood from the above, the fractionation tower is comprised of one or more structured beds. Thus, the height of the primary structured packing/bed utilized within present invention is tailored to achieve a high yield of RTD/TOFA. The RTD/TOFA material recovered in the upper part of the bed may comprise as much as 20% resin acids by weight, even up to 30 wt. %, but it is preferred that the resin acid content of RTD/TOFA is between 1-10% by weight, more preferred in the range of 1-5% by weight of RTD/TOFA compounds. The RTD/TOFA may be further refined by distillation, filtration, cooling etc. before use as feedstock for fine chemicals manufacturing, for use as a fuel, as feed for partial or full decarboxylation in a catalytic bed to produce an oxygen depleted renewable diesel fuel components, or for export for further treatment to diesel range renewable fuel components in a petroleum refinery. It may be mentioned that by the denotation "renewable diesel range fuel components" in here is understood hydrocarbons boiling in the 170-400° C. range. Nevertheless, the primary function of this packing is to separate the bulk RTD/TOFA as top stream and produce RA rich bottom stream.

According to one preferred embodiment of the present invention, the separation of RTD/TOFA and diterpenic acids (resin acids) from a gaseous stream exiting a TFE is achieved in packed bed vacuum fractionation tower connected to the TFE.

Within the TFE unit, which unit is connected to a fractionation tower in all embodiments of the present invention, feed is wiped as a thin-film. The retention time in a TFE is therefore very short and accounts for the preservation of the desirable RTD/TOFA and RA components and hence higher RTD/TOFA and RA yields.

A typical approach to further define the RTD/TOFA fractionation cut is to install a reflux arrangement at the column top which operates in the temperature range 150-220° C. Within the reflux approach, typically a large portion of product is returned into the column in position near the column top end. Generally, higher reflux ratio results into the sharper distillation cut. Advantageously, another structural packing is installed just below the incoming reflux stream. Thus, the packing (i) evenly redistributes the relatively cold reflux stream and (ii) ensures the availability of large surface area which in turn maximizes the reflux effect.

Therefore, according to one specific embodiment of the present invention, the fractionation tower is equipped with a reflux configuration near the column top end. According to another specific embodiment of the present invention, the high end of the stream comprised of components with boiling points 370-420° C. is made more distinct by the selection of suitable reflux ratio. Moreover, according to yet another specific embodiment of the present invention, the homogeneity of the reflux stream entering back the column is achieved by auxiliary structured packing in the column.

In order to achieve effective separation, however, a homogeneous fluid flow throughout the column should also be ensured. When homogeneous fluid flow is realized, the components which are liquid at the present conditions are preferably as fine droplets on packing surface, whereas components that are boiling move as vapours. Homogeneous flow in the column is achieved by appropriate distributors and/or structured packing.

Typically, the heat and corresponding vapours supplied to the packed bed fractionation tower via a reboiler arrangement installed at the bottom of the tower. As it may be understood from the above, one objective within the optimisation of the fractionation tower is minimizing the undesired reactions induced by extensive heating. Thus, the necessary heat and vapours are preferably provided only by the TFE directly connected to the fractionation tower. The liquid volume of the tower is kept minimal. For instance, a heat exchanger supporting the TFE may also be arranged in the system.

The main streams obtained after fractionation in the main tower utilizing packed bed fractionation tower are RTD and a RA rich stream which is further refined to high purity RA subject products of the process disclosed by the present invention.

The further processing of RA is performed in a second fractionation tower (RA polishing tower) according to the present invention. In the second fractionation tower one RTD/TOFA stream being rich of fatty acid components having boiling points in a range of 170-420° C., and one stream of high quality RA and optionally one TOP stream comprising of coloured bodies and other undesirable high boiling point components are obtained. The design of the second fractionation tower is optimised according to the following objectives: (i) maximum yield of RA fraction; (ii) RA fraction with minimum content of FFA and (iii) RA fraction of high (bright) colour grade.

According to the invention the RA polishing tower is a packed bed fractionation tower comprised of one or more structured beds. The tower operates on separate vacuum line providing 0.1-1.0 mbar pressures. The low vacuum levels are facilitated by the absence of the bulk RTD/TOFA fraction. Moreover, the low vacuum levels allow the utilization of essentially the same operating temperatures (150-280° C.) to be used for the RA fractionation and hence decreasing considerably the risks for degradation reactions typical for RA when exposed at high temperatures.

The RA fractionation in the RA polishing tower is achieved within the primary packing (intermediate relative to the other packing beds installed within the tower) of the fractionation tower installed at the middle part of the tower. The packing design provides for the effective separation of the remaining FFA from RA fraction. The separation may also be affected by selection of suitable reflux ratio through the reflux arrangement installed at the tower top along with the structured packing ensuring the homogeneity of the return reflux stream.

The recovered stream comprised of RTD/TOFA components is discharged from a "draw tray" installed below the top packing, whereas the RA stream is discharged from a "draw tray" installed below the intermediate packing.

The necessary heat and vapours are delivered through the stream of RA rich material discharged from the main tower and one or more TFE units preceding the RA polishing tower. The vapours from a TFE are discharged into the polishing tower under a lower packed bed which is optimized to separate all heavy and/or coloured components which in turn are discharged as TOP stream to the TFE from the bottom of the tower. This TFE unit may e.g. be complemented with a falling film evaporator (FFE).

Thus the present invention discloses a process wherein a volatiles free and purified CTO stream is separated into three separate streams or phases, wherein one stream or phase, the RTD/TOFA, is comprised of components with boiling points of about 170-400° C., one stream or phase, the tall oil pitch (TOP), is comprised of components with boiling points over 440° C. and a third stream, comprising diterpenic or resin acids boiling at about 390-440° C. all at atmospheric pressure.

A fourth stream of deodorized and at least partly desulphurized turpentine (including alpha pinene) can optionally be added to a RTD stream after recovery of RTD from the first fractionation tower, said turpentine boiling in the range of 120-200° C. at atmospheric pressure. Turpentine and other low boiling material is added to product RTD in order to decrease density of RTD and increase the portion of components boiling below about 200° C. in the RTD. Turpentine and other low boiling organic components may thus be added to increase portion of C8-C12 carbon molecules in the RTD by as much as 15 wt. %. Preferably, the RTD comprises about 2-15% by weight of C8-C12 turpentine components, more preferred 2-8% by weight of such components.

According to one specific embodiment of the present invention, the total yield of RTD/TOFA based on refined CTO feed is above 50%, such as above 55%, by weight and the total yield of RA is above 15% by weight. According to one specific embodiment, the total yield of RTD/TOFA based on CTO feed is in the range of 55-70% by weight, e.g. around 60 wt. %, and the total yield of RA is in the range of 10-25% by weight, such as around 15 wt. %. The first obtained RTD/TOFA phase from the fractionation tower may represent around 60 wt. % of refined CTO feed, and the second RTD phase from the RA polishing tower around 3 wt. % of refined CTO feed to the first fractionation tower. The first fractionation tower can be controlled and adjusted to achieve the desired RA content of RTD/TOFA normally in the range of 2-30%. The overall yield of RTD can, as is described herein, be further increased by the addition of turpentine's.

In all embodiments of RTD/TOFA and RA recovery from CTO described herein a final high boiling residual product TOP is produced which represents between 10 and 30, or perhaps up to 35%, by weight of the CTO fed to the CTO fractionation. Furthermore the process of the present invention is characterized by low specific energy consumption in comparison to traditional and prior art CTO fractionation processes. The overall energy consumption (hot oil and/or steam) for the fractionation of CTO into RTD/TOFA and RA is lower than about 600 kWh/ton of refined CTO feed, preferably lower than about 500 kWh/ton of refined CTO feed. Current CTO fractionation processes uses well over 1000 kWh/ton specific energy for CTO fractionation.

According to one embodiment of the second aspect of the present invention, there is provided a process for the combined production of RTD and RA from CTO, wherein the refined CTO has been obtained from CTO which has been processed in a pre-treatment step involving CTO washing and separation of impurities, from which pre-treatment step a first refined CTO stream is obtained, said first refined CTO stream then further processed by flashing, steam stripping and/or treatment in a thin-film evaporator in order to remove volatile components from the CTO forming a second refined and substantially volatiles free CTO stream which stream is further processed in a thin-film evaporator in order to separate and remove TOP from a third stream rich in fatty acids and resin acids, which stream is charged to the first fractionation tower for recovery of RTD/TOFA and RA in high yield.

RTD fraction may be combined with lower boiling organic material (boiling point 120-200° C. at atmospheric pressure) including turpentine removed in a tall oil fractionation plant or imported turpentine from a pulp mill. This low density organic material (density from 0.7-0.87 kg/l) is preferably desulphurized and deodorized turpentine and/or tall oil heads (C8-C16 carbon compounds) recovered in a crude tall oil fractionation plant or imported crude turpentine.

RTD produced in accordance with the present invention can be used as an oxygenated refined diesel fuel as such; however RTD is advantageously upgraded into premium diesel fuels by decarboxylation and/or well-known petrochemical deoxygenation/hydrogenation processes. RTD recovered from a fractionation column (with or without addition of turpentine) may advantageously be charged, directly or indirectly, to an additional processing stage located adjacent to the crude tall oil fractionation plant or at a remote location, where at least a portion of the oxygen content of the RTD is decreased via decarboxylation and/or decarbonylation reaction pathways in the presence of a catalyst. Decarboxylation and/or decarbonylation reactions are performed at a temperature in the range of 150-350° C. in fixed bed rectors with one or more catalytic beds. The decarboxylation and decarbonylation reactions are promoted by suitable catalysts. Typical decarboxylation/decarbonylation catalysts include activated (acidic) alumina, zirconia, etc., Fuller earths, carbonate based catalysts and transition metal catalysts. Among transition metal catalysts standard sulphur tolerant catalysts such as NiMo/Al2O3 may be used.

Decarboxylation reactions are endothermic and hydrogen may optionally be injected during decarboxylation to provide heat from exothermal hydrogenation reactions.

Thus the second aspect of the present invention describes a process for recovery of resin acids and a crude tall diesel RTD or TOFA from crude tall oil. The crude tall diesel RTD is further treated under catalytic conditions removing oxygen thereby forming hydrocarbonaceous renewable diesel compounds.

Summary of a Third Aspect of the Invention and Specific Embodiments Thereof

The present invention is also directed to an optimised RTD composition as well as a process for the production of such a composition. The optimised RTD composition according to the present invention comprises 1-30 wt. % resin acid(s) (RA) and 70-95 wt. % fatty acid(s) (FA) and further comprises 1-10 wt. % crude sulphate turpentine(s) (CST) and 0-1 wt. % anthraquinone.

The advantages obtained with the RTD composition according to the present invention are inter alia that the produced crude sulphate turpentine(s) (CST) and optionally the content of anthraquinone is used as high value components, i.e. to increase the total yield of RTD in the process. Furthermore, the CST decreases the density of the RTD mixture and increases the yield of RTD from forest based raw materials. CST produced in the CTO biorefinery described herein as well as imported CST may be added into the RTD composition produced in accordance with the present invention.

According to one embodiment of the present invention there is provided a process for the production of an optimised RTD composition. This process is directed to the production of a refined tall diesel (RTD) composition with lowered density, wherein crude sulphate turpentine(s) (CST) is added to the refined tall diesel (RTD) composition.

According to one specific embodiment, the CST has been produced during separation of volatile components (having boiling points in the range of from 120-250° C.) from CTO or a refined CTO. As mentioned above, CST can also be imported from a Kraft pulp mill and added into a RTD composition according to the present invention.

According to one specific embodiment of this process aspect of the present invention, the volatile components have boiling points below 200° C. The removal of volatile components may e.g. be performed in a process system comprised of steam stripper and/or a thin-film evaporator.

Also this process is advantageously integrated in the other aspects of this invention, i.e. said process is complemented with a first pre-treatment step comprising a CTO wash and separation of impurities for the production of a refined CTO, followed by separation of volatile components having boiling points in the range of from 120-200° C. in the refined CTO for the production of a volatiles depleted tall oil stream. Volatiles depleted tall oil stream is subsequently treated in a thin-film evaporator (TFE) for removal of tall oil pitch (TOP).

The processing in the TFE is performed under vacuum at a temperature of around 300° C. (residence time at this temperature about 2 min). The removal of TOP from the refined tall oil stream in the TFE yields TOP in the range of 10-30 wt. %, and stream of gaseous fatty and resin acids corresponding to about 70-80 wt. % refined tall oil stream charged to the TFE. It should be noted that with respect to the first and third aspects of the present invention, the expression "TFE" may naturally refer to a single TFE but also several TFEs, also several TFEs such as addressed in the second aspect of the present invention.

According to yet another specific embodiment of the present invention, the further refined tall oil stream substantially free from TOP is fed into a fractionation tower where it is fractionated into one stream of refined tall diesel (RTD) being rich in components having boiling points in a range of 170-410° C. and one stream of resin acid with a boiling point in the range of 410-440 is obtained. CST is advantageously added to the RTD after the RTD has been discharged from the fractionation tower, for further improving the yield of RTD and lowering the density of the RTD.

According to yet another embodiment, the total yield of RTD is above 55 wt. %, such as even above 65 wt. %, and the total yield of RA is above 15 wt. % based on CTO fed to the fractionation plant. As an example the first RTD phase obtained from the fractionation tower is around 60 wt. %.

In the final RA polishing fractionation tower RTD is recovered in the upper part and high quality RA is recovered in the lower part. The RTD recovered in the polishing tower comprises substantially fatty acids representing about 1-5% of the total RTD yield. High quality RA with an acid value of 160-180 mg KOH per gram sample recovered from the lower section of the RA polishing tower is exported from the plant. Depending on the market for RA and/or RTD the RA content of the RTD stream recovered from the fractionation tower may be controlled between 2-40%, such as in the range of 2-30%. As is understood, both the first and second RTD stream are combined and exported from the plant with or without addition of CST produced in the plant or imported to the plant.

According to one further embodiment of the present invention, alluded to above, the stream being rich in RA recovered from the fractionation tower is further refined in a RA polishing tower wherein RA is refined to the desired purity (RA content 90 wt. % or higher, FFA less than 4 wt. %, softening point higher than 70° C. and colour between 6-7 on Gardner scale).

DETAILED DESCRIPTION OF THE DRAWINGS

FIG. 1 depicts different steps during the processing of CTO according to the first aspect of the present invention.

In the first step denoted as "CTO wash", the crude tall oil is treated in a series of mixing, reaction and separation steps, where the level of impurities in the resulting stream (denoted as "Refined CTO") is substantially decreased or brought down to the limits of analytical methods used for quantification. In order to achieve impurities removal, the CTO is contacted with a relatively small quantity of water (up to 5 wt. % on CTO basis) containing at least one additive component through intensive mixing at elevated temperatures (just below water boiling point). The mixture thus obtained is directed thereafter into a separation unit able to separate the stream into oil (Refined CTO) and aqueous phases. The water use is dictated by the excellent solubility of CTO impurities in water e.g. residual mineral acid and different inorganic salts and soaps if present. It should be emphasized that the water used should meet certain quality requirements (pH 6.5-7.2; hardness <5° dH; Ca+Mg+Na<1 mg/kg), where typical example is steam condensate. The additive component is typically chelating agent having high affinity towards metal cations and especially transition metal cations. Such additives form very stable and water soluble complexes with these metal cations. Additives with affinity towards broad range of metal cations are preferred in order to keep the process simple where typical examples are but not limited to, citric acid, ethylene-di-amine tetra-acetic acid (EDTA), etc. The separation unit facilitates the phase separation. Especially advantageous units are those using centrifugal force for phase separation. Typically such separation units combine, along with the liquid phase separation, the separation and discharge of eventual solids (such as fibers, non-oil components and lignin). Considering the limited quantity of water addition, separators of clarifier type are of special interest within the present invention. Thus the use of combination of mixing, reaction and separation covers the whole diversity of CTO impurities and ensures their substantial decrease or practical removal.

The aqueous phase is advantageously subjected to a second separation step where the second oil phase is separated from the aqueous phase and other solid impurities. Thus recovered second oil phase can be combined with the refined CTO stream (option depicted by the dashed arrow within the FIG. 1). Another option is to assess the quality of thus recovered second oil phase and if not satisfactory directed it back to the CTO for another pass through the pre-treatment sequence (option depicted by the dotted arrow FIG. 1).

Figure 2:
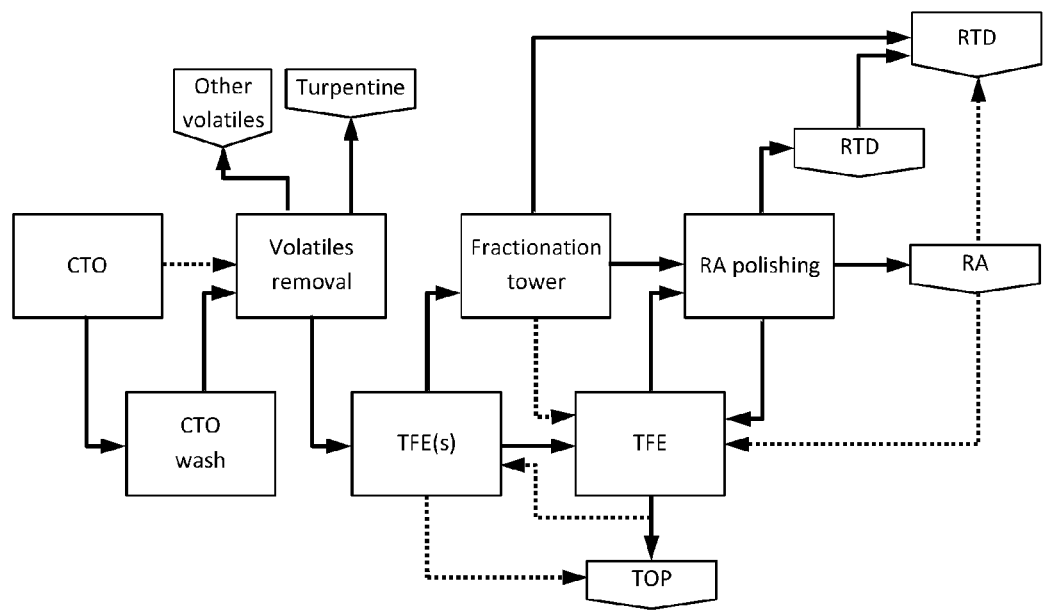

FIG. 2 depicts different steps during the processing of CTO according to the second aspect of the present invention. The full lines indicate basis design for main flows, while dotted lines indicate optional flows.

According to the second aspect of the present invention, the CTO or preferably refined/washed CTO is fed into a process system providing a unit for the separation of volatile components present within CTO. By volatile components is meant components with boiling points below about 170° C. at atmospheric pressure. Typical examples are the components comprising turpentine fraction as well as some carboxylic acids e.g. C12-C14. Other volatiles include water, sulphurous and other gases, etc. The volatiles removal is a necessary requirement considering the following vacuum fractionation steps. The volatiles removal is most advantageously affected in a TFE unit operating at relatively low vacuum (about 50 mbar), which combines effective evaporation of the light components governed by the short diffusion path and short residence time of the refined CTO at elevated temperatures. However, reasonable volatiles removal can also be affected through counter-current contact of refined CTO with stripping media in a packed-bed column at slight vacuum and elevated temperatures.

With the help of one or more TFE units (depitching TFE) the volatiles depleted tall oil stream is fractionated into a liquid heavy bottom fraction, arm of TOFA but still rich in RA and a gaseous phase fraction comprised of TOFA and resin acids. The vapour stream is directed into the main fractionation tower. Careful selection of the operating conditions allows tailoring the boiling point range of the lightest fraction (denoted as RTD product) comprised mainly of FFA and a certain amount of resin acids. The desirable boiling point range for this fraction is between 170 up to about 400° C. at atmospheric pressure. Thus obtained RTD fraction is further utilized for the preparation of high quality diesel range fuel compositions or further refined into TOFA for use in fine chemicals manufacturing. A resin acids rich fraction of reasonably high quality can be obtained as bottom product from the main fractionation tower. The quality of the resin acid fraction is further improved in a separate fractionation tower denoted as "RA polishing" operated at very deep vacuum allowing the use of relatively mild temperatures and hence essentially preserving the resin acids. The RA polishing tower is fed by a stream rich in resin acids discharged from the lower section of the main fractionator and gaseous fraction produced in a TFE unit connected to the RA polishing tower. The TFE is fed by resin acid rich discharge from the TFE or TFEs connected to the main fractionation column. TOP is discharged from the plant from the lower section of this TFE unit. A small portion of high boiling point components is discharged from RA fractionation tower as bottom fraction and discharged in to the TFE connected to the polishing column. The lighter fraction recovered from the upper section of the RA polishing tower comprised of FFA and certain amount of RA is combined with the RTD fraction recovered from the main fractionation tower. Optionally, quote of the RA stream recovered from the RA polishing tower is discharged to the RTD storage or recirculated back to the TFE unit preceding the RA polishing tower).

Figure 3:
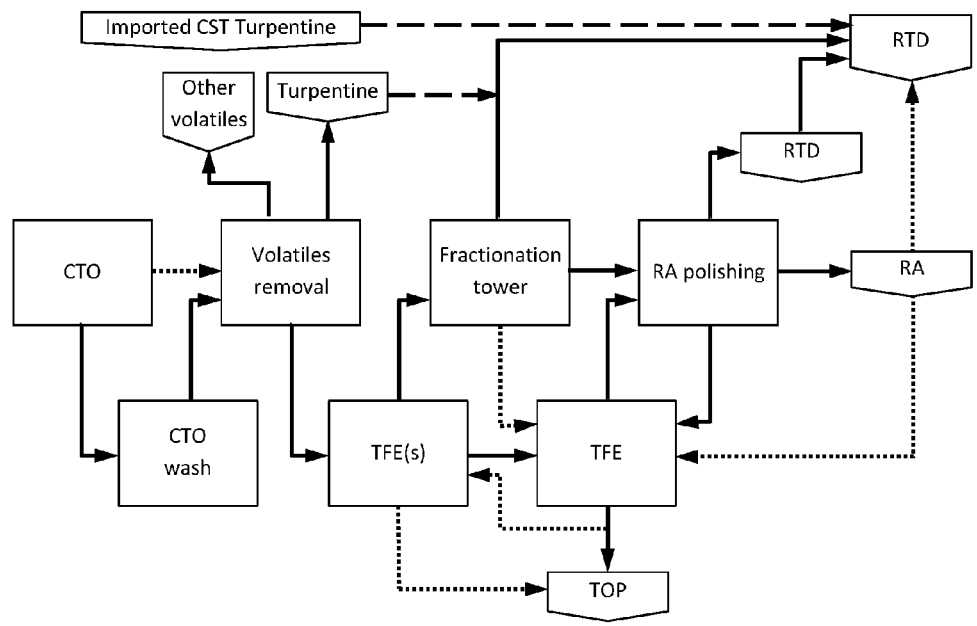

FIG. 3 depicts different steps during the processing of CTO according to the third aspect of the present invention.

Within the third aspect of the present invention the CTO is treated in similar manner as described for the second aspect of the invention. The additional steps here concern (i) the preparation of RTD composition with the addition of a turpentine fraction recovered from CTO during the volatiles removal step and/or (ii) imported CST fraction. Both turpentine (recovered from CTO) and imported CST (dashed arrows FIG. 3) are added to the combined RTD fraction thus forming an improved RTD composition.

The invention claimed is:
1. A process for the pre-treatment of a crude tall oil (CTO), characterized by that said process comprises:
  performing a first pre-treatment step involving performing a CTO wash and a separation of a first oil phase comprising refined CTO and an aqueous phase holding impurities, wherein impurities are removed from the CTO by the removal of the aqueous phase, and performing a second step involving performing a separation of a second oil phase from the aqueous phase for recovery of said second oil phase,
wherein impurities are removed from the CTO by separating off the aqueous phase from said first and second oil phases which first and second oil are being recovered.

2. The process according to claim 1, wherein the CTO is contacted with water in an amount of below 5 wt. % for the CTO wash.

3. The process according to claim 1, wherein at least one additive is added in the first pre-treatment step to bind metal ions within the CTO to produce water soluble metal complexes.

4. The process according to claim 1, wherein the recovered second oil phase is fed into the first oil phase comprising refined CTO.

5. The process according to claim 1, wherein the recovered second oil phase is fed into the CTO.

6. The process according to claim 1, wherein the separation of the first pre-treatment step is performed in a separator unit where the separation is driven by centrifugal force.

7. The process according to claim 1, wherein the separation of the second step is performed by decantation.

8. The process according to claim 1, wherein fibers, salts, residual inorganic acid, transition metals and/or lignin constitute the impurities.

9. The process according to claim 1, wherein the refined CTO is fed into a process system providing separation of volatile components having boiling points below 170° C. present in the CTO to provide a volatiles depleted tall oil stream.

10. The process according to claim 9, wherein the volatiles depleted tall oil stream is fed into a vacuum distillation system to obtain individual high-value fractions of fatty and resin acids.

11. The process according to claim 1, wherein the refined CTO is further treated in a process comprising fractionation under vacuum of the refined CTO into at least one stream of refined tall diesel (RTD) or tall oil fatty acids (TOFA), wherein the stream of RTD or TOFA is deoxygenated forming hydrocarbon compounds in a subsequent step.

12. The process according to claim 11, wherein TOFA with low resin acid content, lower than about 5% by volume, is exported, optionally after further refining, for use in the manufacturing of fine chemicals such as soaps, detergents, adhesives and varnishes.

13. The process according to claim 11, wherein deoxygenation is performed in the presence of hydrogen.

14. The process according to claim 11, wherein the fractionation of CTO is performed under vacuum in at least three units.

15. The process according to claim 11, wherein refined CTO is charged to a first fractionation step for separation of a tall oil fatty acid (TOFA) and resin acid (RA) stream(s), said separation optionally being performed in one or more thin-film evaporators (TFEs) arranged in parallel or in series followed by a second fractionation step wherein a stream rich in RTD or TOFA components having a boiling point at atmospheric pressure in a range of 170-420° C. is separated from a RA rich stream and further followed by a third resin acids purification step performed under deep vacuum.

16. The process according to claim 15, wherein the RA rich stream discharged from the first separation step is further processed in a thin-film evaporator (TFE) for separation of carryover remove tall oil pitch (TOP) components, said RA(s) being further processed under vacuum in a fractionation tower being a RA polishing tower in order to produce high quality RA(s).

17. The process according to claim 15, wherein a RA rich stream is discharged from a lower part of a main fractionation tower in the second fractionation step and charged into a fractionation tower being a RA polishing tower.

18. The process according to claim 16, wherein further processing of RA(s) in a third separation step is performed in a fractionation tower being a RA polishing tower in which one stream being rich in fatty acid components having boiling points in a range of 170-420° C. and one stream being rich in RA(s) are obtained.

19. The process according to claim 1, wherein, from which pre-treatment step of a crude tall oil (CTO) for removal of impurities, a first refined CTO stream is obtained, said first refined CTO stream then being further processed in a steam stripper or a thin-film evaporator to remove volatile components forming and yield a second refined and substantially volatiles free CTO stream which is further processed in a thin-film evaporator to separate and remove a tall oil pitch stream forming and yield a third refined CTO stream charged to a fractionation tower operating under vacuum 1-25 mbar.

20. The process according to claim 11, wherein the refined CTO is further treated in a process comprising fractionation under vacuum of the refined CTO into at least one stream of refined tall diesel (RTD) and wherein crude sulphate turpentine(s) (CST) is added to the refined tall diesel (RTD) composition, for the production of a refined tall diesel (RTD) composition with low density.

21. The process according to claim 20, wherein the CST added has been produced in a step during separation of volatile components having boiling points in the range of from 120-250° C. in a crude tall oil (CTO) or a refined CTO.

22. The process according to claim 21, wherein the volatile components have boiling points below 200° C.

23. The process according to claim 21, wherein the removal of volatile components is performed in a steam stripper and/or a thin-film evaporator.

24. The process according to claim 20, said process also involving the first pre-treatment step comprising a CTO wash and separation of impurities for the production of a refined CTO, then separation of volatile components having boiling points in the range of from 120-200° C. in the refined CTO for the production of a volatiles depleted tall oil stream, then further processing of the volatiles depleted tall oil stream in a thin-film evaporator to produce a further refined tall oil stream and remove tall oil pitch (TOP) from said refined tall oil stream.

25. The process according to claim 24, wherein the further refined tall oil stream is fed into a fractionation tower operating under vacuum in which one stream of refined tall diesel (RTD) stream being rich of components having boiling points in a range of 170-410° C. and one other stream being rich in resin acids (RA) are obtained, and wherein CST is added to RTD after the RTD has been discharged from the fractionation tower.

26. The process according to claim 25, wherein the stream being rich in RA is further processed in one further thin film evaporator to produce a further refined RA rich stream and remove TOP and thereafter feeding the refined RA rich stream into a fractionation tower being a RA polishing tower operating under deep vacuum at 0.1-1.0 mbar in order to separate one stream of fatty acids rich material and one stream of RA in high purity with a fatty acid content below about 4% by volume.

* * * * *